United States Patent
Hsu et al.

(10) Patent No.: US 6,927,201 B2
(45) Date of Patent: Aug. 9, 2005

(54) CAPSULES FOR INCORPORATION INTO DETERGENT OR PERSONAL CARE COMPOSITIONS

(75) Inventors: Feng-Lung Gordon Hsu, Tenafly, NJ (US); Kristina Marie Neuser, Cliffside Park, NJ (US); Robert Joseph Ahart, Mahwah, NJ (US); Deborah Marie Coccaro, Colonia, NJ (US); Peter Anthony Divone, Sr., Bardonia, NY (US)

(73) Assignee: Unilever Home & Personal Care USA division of Conopco, Inc., Greenwich, CT (US)

( * ) Notice: Subject to any disclaimer, the term of this patent is extended or adjusted under 35 U.S.C. 154(b) by 615 days.

(21) Appl. No.: 09/940,778

(22) Filed: Aug. 28, 2001

(65) Prior Publication Data

US 2003/0060378 A1 Mar. 27, 2003

(51) Int. Cl.$^7$ ................................................. C11D 17/08
(52) U.S. Cl. ...................... 510/441; 510/438; 510/349
(58) Field of Search ................................. 510/441, 428, 510/349

(56) References Cited

U.S. PATENT DOCUMENTS

| | | | |
|---|---|---|---|
| 4,369,284 A | 1/1983 | Chen | 524/476 |
| 4,878,775 A | 11/1989 | Norbury et al. | 401/132 |
| 4,906,396 A | 3/1990 | Falholt et al. | 252/174.12 |
| 4,976,961 A | 12/1990 | Norbury et al. | 424/401 |
| 5,013,473 A * | 5/1991 | Norbury et al. | 252/174.13 |
| 5,132,355 A | 7/1992 | Nahlovsky | 524/474 |
| 5,221,534 A | 6/1993 | DesLauriers et al. | 424/78.03 |
| 5,434,069 A | 7/1995 | Tsaur et al. | 435/188 |
| 5,441,660 A | 8/1995 | Tsaur et al. | 252/95 |
| 5,498,378 A | 3/1996 | Tsaur et al. | 264/4.4 |
| 5,589,370 A | 12/1996 | Ratuiste et al. | 264/4.3 |
| 5,733,531 A | 3/1998 | Mitchnick et al. | 424/59 |
| 5,879,694 A | 3/1999 | Morrison et al. | 424/405 |
| 5,972,508 A | 10/1999 | Boeckh et al. | 428/402.2 |
| 6,001,188 A | 12/1999 | Walsh et al. | 134/7 |

FOREIGN PATENT DOCUMENTS

| | | |
|---|---|---|
| EP | 224 389 | 6/1987 |
| EP | 0 273 775 | 7/1988 |
| GB | 2 186 884 | 8/1987 |
| WO | 88/00603 | 1/1988 |
| WO | 92/20771 | 11/1992 |
| WO | 97/24179 | 7/1997 |
| WO | 99/47570 | 9/1999 |

OTHER PUBLICATIONS

Sun Chemicals, *Kraton Polymers Processing Guide*, Jul. 1998.

PCT International Search Report in a PCT application, PCT/EP 02/08640.

* cited by examiner

*Primary Examiner*—Charles Boyer
(74) *Attorney, Agent, or Firm*—Rimma Mitelman

(57) ABSTRACT

Capsules for protecting a benefit ingredient and/or a colorant usefull in detergent or personal care compositions. The benefit agent and/or colorant within the capsule is surrounded by a continuous phase based on a mixture of thermoplastic-type co-polymer and hydrocarbon oil. The continuous phase is preferably transparent. Detergent and personal care compositions containing the capsules are also described.

20 Claims, No Drawings

CAPSULES FOR INCORPORATION INTO DETERGENT OR PERSONAL CARE COMPOSITIONS

FIELD OF THE INVENTION

Capsules having a continuous phase based on a mixture of an oil with a thermoplastic polymer and a discontinuous phase which is itself, and/or contains, a benefit agent and/or a colorant.

BACKGROUND OF THE INVENTION

In many articles of commerce, particularly consumer products, it is desirable to separate certain ingredients, yet have them disposed in a common container. Separation is particularly beneficial where one or more ingredients have negative interactions with each other. For example, in laundry detergents, enzymes are useful in removing stains but it is also best to separate them from other constituents, such as sources of alkalinity and surfactants, especially anionic surfactants like linear alkylbenzene sulfonates or alkyl sulfates. Bleaches, vitamins, perfumes, vegetable oils, plant extracts and ceramides are further examples of ingredients that sometimes need to be separated from the rest of the composition.

A known technique for separating ingredients in a common container includes encapsulation. Encapsulation technology is well known for different applications. Generally, encapsulation includes a medium that surrounds at least one component and thereby provides a barrier between the "encapsulated" component and other components. The barrier is typically temporary and is designed to break down and release the encapsulated material at a desired time, such as at a particular temperature, upon reaction or dissolution with chemicals, or due to mechanical stress. Methods of encapsulation include coacervation, liposome formation, granulation, coating, emulsification, atomization and spray-cooling.

WO 92/20771 discloses particles having a substantially anhydrous core comprising a matrix polymer containing active ingredient, a layer of hydrophobic oil around the core and a shell of polymer around the oil layer. The process for making the particles includes the steps of dispersion in oil of particles of a matrix polymer containing active ingredient, dispersing this dispersion into the aqueous solution and causing a solid polymer shell to form around the droplets of the matrix particles.

Norbury et al. (U.S. Pat. Nos. 4,976,961 and 5,013,473) disclose the addition of a polymer (which may be a polystyrene-polybutadiene-polystyrene block copolymer, e.g. Kraton® 1107) or a wax to an oil phase to increase the viscosity of the oil. The oil-polymer phase forms a core of the Norbury capsule; shell material is formed from another polymer.

Falholt et al. (U.S. Pat. No. 4,906,396, UK 2 186 884, and EP 0 273 775) disclose a protective enzyme system, wherein enzymes are dispersed in a hydrophobic material which is an organopolysiloxane oil or a high molecular weight hydrocarbon including a solid or waxy material. Especially preferred are said to be hydrophobic liquids which had been stabilized by suspending therein hydrophobic solid particles such as hydrophobic silica.

Mitchnick et al. (U.S. Pat. No. 5,733,531) disclose a cosmetic sun-blocking composition containing particles which include a matrix and a UV-attenuating compound incorporated into the matrix. A preferred encapsulating matrix comprises wax. Certain polymeric materials may also be employed.

Ratuiste et al. (U.S. Pat. No. 5,589,370) discloses a process for encapsulation of sensitive materials, the capsule containing an oil dispersion holding an active and an outer polymer shell surrounding the oil dispersion. Tsaur et al. (U.S. Pat. Nos. 5,441,660 and 5,434,069) also disclose a capsule containing an oil dispersion containing an active and the polymer shell surrounding the dispersion. Another patent by Tsaur et al. (U.S. Pat. No. 5,498,378) discloses wax capsules containing a structuring agent which may be a hydrophobic silica, a hydrocarbon material and organophilic clay. An example of a high molecular weight hydrocarbon is given as a hydrocarbon rubber or elastomers.

Morrison et al. (U.S. Pat. No. 5,879,694) discloses transparent stiff gel candles comprising a hydrocarbon oil and a block co-polymer of a thermoplastic rubber (e.g., Kraton® series of polymers).

Despite numerous capsules in the prior art, a problem remains to produce a commercially attractive capsule which is stable—the encapsulated ingredient should not leach out of the capsule upon storage (especially important is the stability of capsules in liquid compositions)—but should release the protected ingredient with ease during normal use. An additional challenge is that the capsules need to be manufactured with relative ease. For instance, in some prior art capsules the melt temperature of the encapsulating material may damage the encapsulated material during the encapsulation process.

An additional, more specific, problem with capsules for consumer products is the manufacture of either transparent or colored capsules. The encapsulating material, e.g. wax, is typically opaque. In such capsules, when the encapsulated ingredient is a colorant, the opaque shell obscures the colored core. Yet, it is frequently desirable to produce a colored capsule to increase the appeal of the consumer product. Including the colorant into the shell material, however, reduces the choice of colorants to oil-soluble colorants (since most encapsulating materials are hydrophobic). Thus, in order to produce colored capsules, it is desirable to encapsulate a water-soluble dye in the transparent shell.

SUMMARY OF THE INVENTION

The present invention includes capsules comprising a continuous and a discontinuous phase, wherein the continuous phase comprises a thermoplastic-type co-polymer and hydrocarbon oil. The discontinuous phase is either itself a benefit agent and/or colorant and/or it comprises a benefit agent and/or colorant. The invention also includes detergent and personal care compositions, preferably liquid, incorporating the capsules.

The following detailed description and the examples illustrate some of the effects of the inventive compositions. The invention and the claims, however, are not limited to the following description and examples.

DETAILED DESCRIPTION OF THE INVENTION

Except in the operating and comparative examples, or where otherwise explicitly indicated, all numbers in this description indicating amounts of material or conditions of reaction, physical properties of materials and/or use are to be understood as modified by the word "about." All amounts are by weight, unless otherwise specified.

For the avoidance of doubt the word "comprising" is intended to mean including but not necessarily "consisting of" or "composed of". In other words the listed steps or options need not be exhaustive.

The term "isotropic" as used herein means a mixture of a block co-polymer and a hydrocarbon oil which has minimum or no turbidity (i.e. light scattering) at 20° C.

The term "continuous" does not necessarily mean "isotropic". The term "continuous" is used herein to denote the phase which is predominant in volume during emulsification or dispersion of discontinuous phase in the continuous phase.

The term "hydrocarbon oil" as used herein means a hydrocarbon oil having a maximum viscosity of about 10 kg/(m)(sec), preferably no greater than about 5 kg/(m)(sec).

The term "wax" as used herein means a hydrophobic material which is a solid at 20° C. By "solid" is meant the ingredient is not mobile at 20° C.

The term "immiscible" as used herein means that discontinuous phase does not form a single phase with the continuous phase, i.e. the two phases form a partition between phases.

The term "transparent" as used herein includes both transparent and translucent and means that an ingredient, or a mixture, or a phase, or a capsule, or a composition, or a package according to the invention preferably has a transmittance of more than 25%, more preferably more than 30%, most preferably more than 40%, optimally more than 50% in the visible part of the spectrum (approximately 410–800 nm).

Alternatively, absorbency may be measured as less than 0.6 (approximately equivalent to 25% transmitting) or by having transmittance greater than 25% wherein % transmittance equals: $1/10^{absorbancy} \times 100\%$. For purposes of the invention, as long as one wavelength in the visible light range has greater than 25% transmittance, it is considered to be transparent/translucent.

The capsules of the invention comprise a discontinuous phase containing an ingredient to be encapsulated, and a continuous phase surrounding the discontinuous phase.

Continuous Phase

The continuous phase of the inventive capsules comprises a hydrocarbon oil and a block co-polymer containing at least one rigid block and at least one flexible block. The mixture of the hydrocarbon oil and the block co-polymer according to the present invention is isotropic at 20° C. It should be understood that since the co-polymer is not pourable at 20° C. (indeed, it is solid), it may be difficult to combine the co-polymer with the oil at 20° C. to ascertain whether the mixture is isotropic. According to the present invention, a mixture may be formed at any suitable temperature at which the liquefied co-polymer forms an isotropic liquid mixture with the oil. The copolymer/oil mixtures suitable for use in the present invention, however, remain isotropic after cooling to 20° C.

Preferably, especially in the case of colored capsules, the continuous phase is transparent and uncolored.

Block Co-polymer

In one embodiment of the invention, the co-polymer employed in the continuous phase of the inventive capsules is selected from the group consisting of a triblock co-polymer, radial co-polymer, and multiblock co-polymer, the co-polymer comprising at least one triblock with a structure: rigid block—flexible block—rigid block. Preferably the rigid block is styrene-type polymer, and the flexible block is rubber-type polymer. By virtue of employing the rigid-flexible-rigid block co-polymer, the viscosity of the oil is increased, and the hardened continuous phase is formed, yet the resulting capsule is sufficiently soft and friable to release the discontinuous phase in normal use. The co-polymer blends uniformly with oil at a temperature which is much lower than the melting point of wax, thus allowing for encapsulation of temperature-sensitive ingredients, e.g. bleach, perfume, enzyme, vegetable oil, etc. A further advantage of using the co-polymer is that it is not necessary (although possible) to use a surfactant in preparing a uniform distribution of the discontinuous phase in the continuous phase; the avoidance of the surfactant makes the encapsulation process easier and cheaper. Furthermore, the absence of surfactant improves the stability of the encapsulated ingredient, since the surfactant provides a potential channel of penetration for an external environment.

The preferred co-polymers are transparent and uncolored, in order to attain a transparent and uncolored continuous phase.

Examples of suitable co-polymers include but are not limited to those that are described in Morrison et al. (U.S. Pat. No. 5,879,694) hereby incorporated by reference herein.

A triblock polymer, or a mixture of triblock polymer with diblock polymer, are preferred, since they may more easily form robust capsules, without the addition of a hydrophobic solid, yet resulting in capsules with a transparent shell.

Each of the triblock, radial block and/or multiblock copolymers in the invention contains at least two thermodynamically incompatible segments. By the expression thermodynamically incompatible with respect to the polymers, it is meant that the polymer contains at least two incompatible segments, for example at least one hard and one soft segment. In general, in a triblock polymer, the ratio of segments is one hard, one soft, one hard or an A-B-A copolymer. The multiblock and radial block copolymers can contain any combination of hard and soft segments, provided that there are both hard and soft characteristics. In the optional diblock copolymer, the blocks are sequential with respect to hard and soft segments.

Commercially available thermoplastic rubber type polymers which are especially useful in forming the compositions of the present invention are sold under the trademark Kraton® by Shell Chemical Company. The Kraton® rubber polymers are described as elastomers which have an unusual combination of high strength and low viscosity and a unique molecular structure of linear diblock, triblock and radial copolymers. Each molecule of the Kraton® rubber is said to consist of block segments of styrene monomer units and rubber monomer and/or comonomer units. Each block segment may consist of 100 or more monomer or comonomer units. The most common structure is the linear ABA block type; styrene-butadiene-styrene (SBS) and styrene-isoprene-styrene (SIS), which is the Kraton® D rubber series.

A second generation polymer of this general type is the Kraton® G series. This copolymer comprises a styrene-ethylene-butylene-styrene type (S-EB-S) structure. The Kraton® G series is preferred in the practice of the invention, as the copolymers of this series are hydrogenated and thus more thermally stable; that is, decomposition is less likely to occur during blending of the G series polymers with the oil (the D series polymers having unsaturation within the rubber block). The Kraton® G rubbers are indicated as being compatible with paraffinic and naphthenic oils and the triblock copolymers are reported as taking up more than 20 times their weight in oil to make a product which can vary in consistency from a "Jello®" to a strong elastic rubbery material depending on the grade and concentration of the rubber.

The optionally blended diblock polymers include the AB type such as styrene-ethylenepropylene (S-EP) and styrene-ethylenebutylene (S-EB), styrene-butadiene (SB) and styrene-isoprene (SI).

The ABA structure of the Kraton® rubber molecule has polystyrene endblocks and elastomeric midblocks. This series of polymers is indicated as being a compounding ingredient or additive in adhesives, sealants and coatings, asphalt modification for roads and roofing, polymer modification, thermoset modification, and oil modification including use as viscosity index improvers, greases and gels. Certain grades of the Kraton® D series are also indicated as being useful as viscosity modifiers for formulating multi-grade motor oils.

International Patent Application No. WO88/00603, published Jan. 28, 1988, by Francis et al. describes block copolymers which can be used as one or more components in the present invention. These block copolymers are described as gels or gelloid liquid extended polymer compositions which can comprise an intimate mixture of a block copolymer containing relatively hard blocks and relatively elastomeric blocks. The additional polymer or copolymer material has at least partial compatibility with, and a higher glass transition softening or melting temperature than, the hard blocks of the block copolymer. The copolymer additionally has at least 500 parts by weight of extender liquid per 100 parts of the block copolymer, the liquid being present to extend and soften the elastomeric blocks of the block copolymer. The extender liquid can be a hydrocarbon oil and/or a synthetic oil. The entire disclosure of this published application is incorporated herewith.

International Patent Application No. WO88/00603 also refers to European Patent Application No. 224389 of Garmarra et al, published Jun. 3, 1987. This European patent application discloses styrene-diene block copolymer compositions and in particular discloses a mixture of triblock copolymers and a hydrocarbon oil, wherein the mixture of triblock copolymers comprises a triblock polymer having (a) styrene to ethylene-butylene ratio of 14 to 30 styrene blocks to 70 to 86 ethylene-butylene blocks, and (b) ethylene-butylene ratio of 31 to 35 styrene blocks to 65 to 69 ethylene-butylene blocks, and wherein the ratio of copolymer A to copolymer B is from about 15 to 85 to about 85 to 15. These compositions are said to be particularly useful as sealing materials. The disclosure of European Patent Application No. 224389 is also incorporated herein by reference.

U.S. Pat. No. 5,221,534 discloses gels having a mineral oil and blends of di- and triblock copolymers. These gels are useful for health and beauty aid compositions. These health and beauty aid compositions contain at least two diblock or triblock copolymers and an effective amount of one or more cosmetic ingredient. Preferred compositions in U.S. Pat. No. 5,221,534 contain both diblock and triblock copolymers, with the polymer blend being from about 5 to 95 wt % of diblock polymer to 95 to 5 wt % of triblock polymer. The entire disclosure of U.S. Pat. No. 5,221,534 is also incorporated herein by reference.

U.S. Pat. No. 4,369,284 describes a transparent gel prepared from triblock copolymers and oils, including food and technical grade white petroleum mineral oils. The triblock copolymers therein give specific styrene end blocks to ethylene and butylene center blocks. The end block to ethylene and butylene center block ratio is given as being between 31:69 and 40:60. It is preferred under the present invention, however, that the end block to ethylene and butylene center block ratio be less than 31:69. The polymer content in the Examples of U.S. Pat. No. 4,369,284 is from 5.9 to 25 percent. The disclosure of U.S. Pat. No. 4,369,284 is incorporated herein in its entirety.

U.S. Pat. No. 5,132,355 discloses polyethylene block copolymers of the A-B-A type, where in A is a "hard" block and B is a "soft" block. The gel made from this diblock copolymer is disclosed as being useful for complex molded candles when used with paraffin wax.

The preferred polymer is a triblock polymer of the Kraton® G type, in particular Kraton® G-1650. Kraton® G-1650 is an SEBS triblock copolymer which has a specific gravity of about 0.91, and is said to have a tensile strength of about 3.45 newton/m2 as measured by ASTM method D-412-tensile jaw tester separation speed 25.4 cm/min. The styrene to rubber content of Kraton® G-1650 is said by the manufacturer to be about 29:71, and the Brookfield viscosity is about 8 kg/(m)(sec)(toluene solution, at 25° C., 25% w). The Shore A hardness is about 75.

For making the transparent capsules, preferably a mixture of Kraton® 1650 with Kraton® 1702 is employed, even though Kraton® 1650 is sufficient on its own. The mixture may be preferred in some cases, in order to increase the hardness of the capsules, while preserving transparency.

In a second embodiment of the invention, the diblock co-polymer may be employed (having rigid-flexible blocks), even in the absence of a triblock or radial co-polymer. Kraton® 1702 is a diblock co-polymer (styrene-ethylene/propylene). The properties of Kraton® 1702 make it more suitable for use as a viscosity modifier in making an emulsion. According to the second embodiment of the invention, when using Kraton® 1702, in the absence of other copolymers, a hydrophobic solid is added, in order to form capsules. Kraton® 1650, on the other hand, forms a gel, when mixed with oil. When using the mixture of two Kraton® polymers, the weight ratio of Kraton® 1650 to Kraton® 1702 is generally from 1:10 to 10:1, more preferably from 3:1 to 7:1, most preferably from 2:1 to 5:1, and optimally from 1:1 to 4:1.

The block co-polymer is employed in the inventive capsules generally in an amount of from 0.1% to 15%, more preferably from 0.5% to 10%, most preferably from 0.5% to 7%, and optimally from 1% to 4%, by weight of the continuous phase.

Hydrocarbon Oil

According to the present invention, any hydrocarbon oil may be employed, as long as: (1) it is an oil at room temperature (i.e., has a maximum viscosity of about about 10 kg/(m)(sec), preferably no greater than about 5 kg/(m)(sec)) and (2) it forms an isotropic mixture with the block co-polymer described above.

The isotropicity of the mixture may be determined by measuring light scattering (such as by turbidity measurement). If the turbidity is minimum or none at 20° C., the mixture is isotropic. Suitable apparatus for measuring turbidity is UV-visible spectrophotometer (turbidity is measured in the visible light range), e.g. HP-8452: mixtures having a transmittance of at least 50%, preferably at least 70% and above are suitable for use in the present invention.

Natural or synthetic hydrocarbon oil or mixtures thereof may be employed. Generally, the hydrocarbon oil may be a paraffinic oil, a naphthenic oil, vegetable oil, mineral oil or the like. Examples include but are not limited to mineral oil, castor oil, vegetable oil, corn oil, peanut oil, jojoba oil, 2-ethylhexyl oxystearate (and other alkyl oxystearates), acetylated lanolin alcohol, alkyl palmitates such as isopropyl palmitate, 2-ethylhexyl palmitate, glycerol triacetates, diisopropyl adipate, dioctyl adipate (and other alkyl adipates), isopropyl myristate, C12 to C15 alcohol benzoates, and the like.

Most preferably, the oil is mineral oil, because it is both economic and most compatible with the block co-polymer.

Preferably, when Kraton® series block co-polymers are employed (i.e., styrene-elastomer block co-polymers), the oil is essentially free of silicone-containing oils, in order to obtain optimum isotropic mixtures. By "essentially free" is meant that in the Kraton®/oil continuous phase, the amount of silicone oil is preferably less than 2%, by weight of the continuous phase, more preferably less than 1%, most preferably less than 0.5% and optimally is 0%.

The preferred oils are transparent and uncolored, in order to attain a transparent and uncolored continuous phase (although colored continuous phase is also included within the scope of the invention).

Optional Preferred Ingredients in the Continuous Phase

A preferred ingredient for the continuous phase, in order to strengthen the capsules is a hydrophobic solid. This ingredient forms an isotropic mixture with co-polymer/oil mixture when heated, but, on cooling, the mixture will no longer be isotropic. Thus, the isotropicity of the copolymer/oil (and thus the suitability of the chosen oil) should be tested in the absence of the hydrophobic solid. Furthermore, if transparent capsules are desired, the addition of a hydrophobic solid is not preferred. Examples of suitable hydrophobic solids include, but are not limited to wax, microcrystalline wax, fatty acid, hydrophobic silica, pigment (e.g., titanium dioxide), fatty alcohols, thermoplastic homopolymers (preferably, polymers with melting point less than 95° C., to prevent boiling-out of the aqueous phase) such as polyethylene, polypropylene, and mixtures thereof.

Preferably, the hydrophobic solid is selected from paraffin wax, beeswax, micro-crystalline wax, polyethylene, polypropylene, most preferably paraffin wax or beeswax, due to their low price and easy processability.

The continuous phase generally includes from 0.1% to 60%, more preferably from 5% to 50%, most preferably from 10% to 40%, and optimally from 30% to 35% of the hydrophobic solid, in order to achieve the best balance between stength of the capsules and their friability in use (% by weight of the total continuous phase).

Discontinuous Phase

The discontinuous phase of the inventive capsules is itself and/or comprises a benefit agent and/or a colorant. In some embodiments of the invention, the discontinuous phase is itself a benefit agent, e.g. a vegetable oil, such as sunflower seed oil, in personal care compositions. In other embodiments, the discontinuous phase is itself a colorant (e.g. a solid pigment). Still in other embodiments the discontinuous phase serves as a vehicle for a benefit agent and/or colorant. And still in other embodiments of the invention the discontinuous phase may itself be a benefit agent and/or colorant and also further include an additional benefit agent and/or colorant. According to the present invention, the discontinuous phase is immiscible with the continuous phase, to prevent the exposure of the discontinuous phase to the environment outside the capsule. The discontinuous phase may be a solution (aqueous or oil), an oil, an emulsion, a dispersion or a solid. The preferred form of the discontinuous phase is an oil or a solution (oil or aqueous solution), due to the relative ease of incorporation of the oil or the solution into the continuous phase. The capsules may include more than one discontinuous phase.

If the additional benefit agent/colorant is oil-soluble, than an oil is chosen to carry the benefit agent/colorant in the discontinuous phase; if the benefit agent/colorant is water-soluble, than the discontinuous phase is an aqueous solution. Of course, as mentioned above, solids may be employed, without making a solution.

The discontinuous phase is present in an amount of from 0.01 to 45%, more preferably from 5 to 45%, most preferably from 10 to 40%, and optimally from 20 to 35%, (% by volume of the capsule) in order to deliver sufficient benefit agent/colorant, provide adequate protection for the benefit agent/colorant and to maintain the ease of processing.

Most preferably, the capsule contains both the benefit agent and the colorant, within a transparent shell, to provide a visual signal to the consumer that a composition contains an additional beneficial ingredient.

Benefit Agent

The choice of the benefit agent depends largely on whether the final consumer composition is a detergent composition or a personal care composition. As mentioned above, the discontinuous phase itself may represent a benefit agent, so it is not necessary that an additional benefit agent be present. Thus, an additional benefit agent may be present in an amount of from 0 to 100%, preferably 0.01 to 50%, more preferably 0.1 to 20%, by weight of the discontinuous phase.

Typical additional benefit agents include, but are not limited to a bleach, a bleach precursor, a surfactant, an enzyme, a whitening agent, a fabric softener, an anti-wrinkle compound, a dye fixative, dye transfer inhibitors, anti-redeposition polymers, soil release polymers, an anti-foam agent, a perfume, a silicone oil, a vegetable oil, a vitamin, a plant extract, a hydroxy acid, an anti-oxidant, an anti-bacterial agent, a moisturizer, and mixtures thereof.

Benefit agents are described in further detail below, under Detergent Compositions and Personal Care Compositions sections.

Colorant

The colorant may be a dye or a pigment. Dyes are preferable, since they are water-soluble and thus are more easily incorporated into capsules, compared to pigments which are typically not water-soluble. In one preferred embodiment of the invention, a water-soluble colorant is employed. Most preferably, a water-soluble dye is encapsulated, alone or in the mixture with a benefit agent, within a transparent, uncolored continuous phase.

Capsule Shape and Size

The preferred capsules are substantially spherical, particularly, when incorporated into transparent composition and/or transparent package, in order to provide a pleasing, commercially attractive appearance. Other shapes, however, such as star, disk, square and oval, are possible.

The size of the capsules is such as to render them suitable for incorporation into detergent or personal care compositions. Typical size range is from 300 $\mu$m to 5,000 $\mu$m, more preferably from 500 $\mu$m to 3,000 $\mu$m, most preferably from 800 $\mu$m to 1,600 $\mu$m, to provide visibility while ensuring uniform suspension.

Process of Making the Capsules

The inventive capsules may be prepared by any known encapsulation processes. Preferably, however, the capsules are prepared by the following process.

The preferred process comprises immersing droplets of an emulsion or a dispersion containing the continuous and discontinuous phases into an aqueous curing solution containing a high HLB surfactant and/or a super-wetting agent.

In the first step of the inventive process, an emulsion or dispersion is prepared by mixing the continuous and discontinuous phases, the latter being or containing the ingredient to be encapsulated, e.g. bleach solution or a vegetable oil. In the preferred embodiment, the co-polymer is melted, mixed with oil, then the discontinuous phase is added, with stirring (agitation), to ensure uniform mixing of the ingredients. The resulting emulsion/dispersion is preferably kept at a temperature in the range from 40° C. to 95° C. Most preferably, the use of direct heat is avoided. A most preferred temperature range is from 60° C. to 75° C.

The resulting emulsion/dispersion is directed, either as a stream, or dripping, into the curing solution containing a surfactant with a relatively high HLB value and/or a super-wetting agent, whereby the discrete capsules are formed. Optionally, pressure may be employed in ejecting the stream, in order to ensure that the stream penetrates the surface of the curing solution. The curing solution may also be chilled, stirred, and/or pressurized. The curing solution is prepared by combining water and at least one surfactant with a high HLB value and/or a super-wetting agent.

The surfactants for the curing solution are selected from the group consisting of high HLB (7 to 25, preferably 10 to 20, most preferably 12 to 16) surfactants, preferably linear and branched nonionic such as Neodol® 25-12, 25-9 and Tergitol® 15-S-9. In the most preferred embodiment, the surfactant is Neodol® 25-12, which has a carbon chain length between 12 and 15, with 12 ethylene oxide groups per molecule.

The surface tension modifying agent or super-wetting agent is a highly efficient, low surface energy surfactant. Examples of super-wetting agents are as follows:

| Super-wetting Agent | Supplier | Chemical Description |
|---|---|---|
| Zonyl ® FSO | duPont | Fluoro chemical with ethylene glycol |
| Fluorad ® | 3M Company | Fluorinated alkyl alkoxylate |
| DC Q2 | Dow Corning | Polyoxy ethylene modified polydimethyl siloxane |
| Tergitol ® 15-S | Union Carbide | Mixture of linear secondary alcohols reacted with ethyleneoxide |
| Surfynol ® TG | Air Products & Chemicals | 2,4,7,9-teramethyl-5-decyne-4,7-diol |
| Makon ® OP-9 | Stepan Chemical | Octyl phenol with 9 moles of ethylene oxide |
| Fluowet ® OTN | Hoechst Celanese | Fluoroaliphatic oxyethylate |
| Forafac ® 1157N | Atochem | Polyfluoroalkyl betaine |
| Silwet ® L-77 | OSI Specialty | Polyalkylene oxide modified heptamethyltrisiloxane |

The most preferred super-wetting agent is Silwet® L-77 due to its ready availability and optimum performance.

The constituents in the curing solution are preferably present in the following ranges: water, 60% to 99%, most preferably 80% to 95%; surfactant and/or a super-wetting agent, 1% to 40%, most preferably 5% to 15% (all by weight of the curing solution).

In the preferred embodiment, the curing solution comprises both the high HLB surfactant and the super-wetting agent.

The super-wetting agent is preferably added as a pre-diluted solution by dripping along, as close to the capsule formation as possible, so that the super-wetting agent is on the surface of the curing solution.

The preferred curing solution contains a super-wetting agent generally in an amount of from 0.1 to 40%, more preferably from 1 to 20%, most preferably from 2 to 10%, and optimally from 3 to 7% (% by weight of the curing solution).

The curing solution is preferably kept at a temperature in the range from 0° C. to 50° C. The most preferred temperature range is from 10° C. to 30° C.

In one preferred embodiment, the emulsion/dispersion of the continuous and discontinuous phases is caused to flow (preferably, under pressure) to form a stream which is directed into the curing solution. The stream breaks up into capsules within the curing solution. The stream can be defined by temperature, velocity, width and distance from the upper surface of the curing solution. The size of the orifice through which the stream is directed and the pressure with which it is ejected will also affect the nature of the stream. In a preferred embodiment, the following operating parameters were found to produce capsules in the range of 200 $\mu$m to 2500 $\mu$m: emulsion temperature: 54–85° C.; vessel pressure: 0–1.05 kg/cm2, most preferably 0.3–0.6 kg/cm2; nozzle distance from curing solution: 2.5–20 cm, most preferably 17.5 cm; nozzle orifice diameter: 0.0125–0.25 cm; curing solution temperature: 0–50° C.

In an alternative preferred method for forming the capsules, the emulsion/dispersion is delivered to the curing solution by a plurality of nozzles: the emulsion is allowed to drip under the static head or the pressure. The dripping forms capsules upon contact with the curing solution. The size of the nozzle openings and the height of the liquid in vessel ("static head") containing the emulsion and the distance from the curing solution all play a part in the ultimate size of capsules.

In each embodiment, the curing solution is continually agitated during the emulsion addition, in order to distribute the formed capsules and keep the surface in motion.

In each of the above processes, the droplets/capsules advantageously have a density greater than that of the curing solution. As such, the formed capsules fall to the bottom of the receiving vessel and do not interfere with new droplets/capsules as they contact the surface of curing solution. Preferably, the density of the capsules is at least 1.0, most preferably from 1.01 to 2. Suitable methods for increasing the density include, but are not limited to the addition of solid inorganic material, (e.g. sugar or sorbitol), or any high density solute to the discontinuous phase of the emulsion.

Without being bound by theory, it is believed that the outer, hydrophobic surface of capsules attracts the hydrophobic portions of the surfactant molecules in the curing solution, thereby leaving the hydrophilic portions of the surfactant molecules extending from the outer surface of the capsules. Assuming this to be true, the capsules naturally repel each other due to hydrophilic molecule portions extending from the hydrophobic "shell". During processing this is advantageous because the capsules remain separate in solution.

In the final, optional, step of the process, in order to make the process continuous, the capsules may be collected out of the curing solution. If the capsules have density higher that that of the curing solution (i.e., higher than the density of water), then the vessel holding the curing solution may have one or more openings in the bottom of the vessel, for the capsules to drain out. The vessel volume may be continuously made up with a fresh curing solution.

If the capsule density is lower than that of water, then the capsules may be collected off the top of the solution by floating the top of the solution off into a collection vessel. Again, the vessel volume may be continuously made up with a fresh curing solution. When this method of collection is employed, it is particularly important that the droplets penetrate the solution surface (e.g., the pressure is employed in forming droplets and/or a super-wetting agent is employed), so that the capsules are formed before the top layer of the curing solution is collected.

The capsules may be directly incorporated into a detergent or personal care composition, or the capsules may be stored in the form of a concentrated stock solution, which generally includes from 10 to 95% of water, more preferably from 20 to 80%, most preferably from 30 to 70%, and optimally from 35 to 60%, in order to attain the best balance between maximum concentration of the capsules and the stock's viscosity, the latter affecting its pumpability (% by weight of the total stock solution).

Detergent Compositions

Various detergent compositions include, but are not limited to laundry compositions, hard surface cleaners, dishwashing compositions. Detergent compositions may be in the form of powders, tablets, liquids, gels, water-soluble pouches and any combinations thereof.

Preferred detergent compositions are liquids or gels and, especially, aqueous-based compositions, since such compositions present a particular challenge, when benefit agents, e.g. bleaches or perfumes, need to be included. Thus, preferred liquid detergent compositions include from 10 to 80%, preferably from 30 to 70%, most preferably from 50 to 65% of water. Liquid detergent compositions generally have a pH from 6 to 13, preferably from 7 to 9.

The capsule concentration in the detergent composition is determined by the nature and/or amount of the benefit agent and/or colorant, and the size of the particles. Detergent compositions generally include from 0.01 to 20%, more preferably from 0.1 to 10%, most preferably from 0.2 to 5%, and optimally from 0.4 to 3%, of the inventive capsules (% by weight of the composition).

Preferred laundry compositions comprise, in addition to the inventive capsules, a surfactant, in an amount from 1 to 70% more preferably from 10 to 50%, most preferably from 15 to 35%, and optimally from 15 to 30% (% by weight of the laundry composition). Suitable detergent and laundry surfactants are well known to one of ordinary skill in the art and may in general be chosen from anionic, nonionic, amphoteric, and cationic surfactants. Preferably, the surfactant in the laundry compositions is anionic and/or nonionic, especially linear alkylbenzene sulfonate, alkyl ether sulfate, alcohol ethoxylates and mixtures thereof.

In addition to the surfactant and the inventive capsules, the preferred laundry composition may include one or more well-known laundry ingredients, such as builders (from 0.1 to 40% for powders, from 0.1 to 20% for liquids), anti-redeposition agents, fluorescent dyes, perfumes, soil-release polymers, colorant, enzymes, etc.

Preferred detergent compositions according to the invention contain inventive capsules with encapsulated bleach or bleach system, preferably in aqueous solution. Any bleach suitable for detergent application may be included. Examples include, but are not limited to chlorine bleaches, peracids, bleach precursors, alone or with oxygen sources.

Bleach capsules for detergent compositions generally include from 0.5 to 15%, more preferably from 1% to 10%, most preferably from 3% to 8% and optimally from 4% to 7%, of a bleach, in order to deliver an optimum benefit for minimum cost (% by weight of detergent composition).

Preferably, the detergent composition is a transparent composition containing transparent or colored capsules, and packaged in the clear/transparent package.

Personal Care Compositions

Personal care compositions according to the present invention may be solid or liquid, and include products which are rinsed off after application (e.g., shower gels, shampoos or soap bars) and product that are left on after application (e.g., cosmetic lotions, gels and creams). Various personal care compositions include, but are not limited to soap bar compositions, facial or body cleansing compositions, shampoo compositions, conditioner compositions, and cosmetic compositions. Personal care compositions may be in the form of solution, lotion, cream, gel, solid and any combinations thereof.

Preferred personal care compositions are liquids, gels and, especially, aqueous-based compositions, since such compositions present a particular challenge, when benefit agents, e.g. vitamins or vegetable oils, need to be included. Thus, preferred liquid personal care compositions include from 0.1 to 99% preferably from 2 to 80%, most preferably from 10 to 60%, of water. Liquid personal care compositions generally have a pH from 3 to 8, preferably from 5 to 7.

The capsule concentration in the personal care composition is determined by the nature and/or amount of the benefit agent and/or colorant. Personal care compositions generally include from 0.01 to 20%, more preferably from 0.1 to 10%, most preferably from 0.2 to 5% and optimally from 0.4 to 3%, of the inventive capsules (% by weight of the composition).

Preferred personal care compositions comprise, in addition to the inventive capsules, a cosmetically acceptable vehicle, in an amount from 0.1 to 70%, more preferably from 3 to 85%, most preferably from 5 to 95% and optimally from 10 to 99% (% by weight of the composition). Suitable vehicles are well known to one of ordinary skill in the art and may in general be chosen from isotropic liquid formulas or structured liquid formulas. Preferably, the vehicle in the personal care compositions is structured liquid formulas especially lamellar forming (structured) liquid formulas.

In addition to the vehicle and the inventive capsules, the preferred personal care composition may include one or more well-known personal care ingredients, such as viscosity builders (from 0.1 to 30%), pH controllers (stabilizers) (from 0.005 to 20%).

Preferred personal care compositions are personal wash compositions, wherein the capsules contain a combination of a benefit agent and a colorant, with the benefit agent chosen from vitamins, antibacterial agents, vegetable oils, and mixtures thereof.

Vitamins include, but are not limited to vitamins A, E, C. Anti-bacterial agents include, but are not limited to Triclosan®. Vegetable oils include but are not limited to sunflower seed oil, safflower oil. The personal wash compositions include, in addition to the capsules and the vehicle, a surfactant, especially Tegobetaine® (Cocamidopropyl Betaine). The surfactant is included generally in an amount form 0.1 to 10%, most preferably form 1 to 3%, and optimally from 2 to 6% (% by weight of the total composition).

Preferably, the personal care composition is a transparent composition containing transparent or colored capsules, and packaged in the clear/transparent package.

The following specific examples further illustrate the invention, but the invention is not limited thereto.

Suppliers and chemical description of the ingredients used in the examples are summarized in the following table:

| Trade Name (if appropriate) | Chemical Name | Supplier |
|---|---|---|
| Kraton ® 1650 | Styrene-(ethylene-Butylene)-Styrene tri-block co-polymer | Shell |
| Kraton ® 1702 | Styrene-(Ethylene-Propylene) di-block co-polymer | Shell |
| Sorbitol | D-Glucitol | SPI Polyols |

-continued

| Trade Name (if appropriate) | Chemical Name | Supplier |
|---|---|---|
| Neodol ® 25-9 | Nonionic surfactant: Alcohol Ethoxylate, C12–C15 9 Ethylene oxide groups HLB = 13.1 | Shell |
| Blue Dye | Sandolan Blue E-HRL powder 120 | Sandoz Chemicals |
| Silwet ® L-77 | Polyalkylene oxide modified hertamethyltrisiloxane 84%, and Allyloxypolyethylene glycol methyl ether 16% | OSI Specialties |
| | Mineral Oil | Fischer Scientific |
| 1218 ® Wax | Petroleum, Hydrocarbon, paraffin Wax | IGI |
| Menthol Oil | Hexahydrothymol | Irvine Boody |
| | Vitamin E | BASF |
| Triclosan ® | 2,4,4 Trichloro-2Hydroxydiphenyl Ether | Ciba |
| | Sodium Hypochlorite | Clorox |
| Properase ® 1600 L | Protease | Genencor International, Inc |
| | Sunflower Seed Oil | Welch, Holmes and Clark Co., Inc. |

EXAMPLE 1

Capsules within the scope of the invention were prepared. One of the problems with encapsulation has been stability, especially enzyme stability. In many examples below, sorbitol has been substituted for enzymes due to their like densities and hydrophilic nature.

| Capsule formulation | |
|---|---|
| 2% Kraton ® 1702 | 35% |
| Bowax ® 800 | 20% |
| 70% Sorbitol aqueous solution | 45% |

2% Kraton® 1702 liquid gel was prepared by mixing 2 parts of Kraton® 1702 and 98 parts of mineral oil and heated to 76.7° C. until it became an isotropic liquid gel. 35 parts of this prepared 2% Kraton® 1702 gel was mixed with 20 parts of Bowax® 800 at 60° C. and followed by mixing in 45 parts of 70% sorbitol aqueous solution to form an emulsion. This emulsion was used to form capsules in an aqueous curing solution containing 1% Silwet® L77.

Equipment Used:

Re-circulating encapsulation unit powered by a peristaltic pump. Lightening mixer was used to create movement in water bath so capsules didn't land on one another.

Results were capsules that were discrete: they didn't stick together when they came in contact with one another.

EXAMPLE 2

Capsules within the scope of the invention were prepared.

An encapsulation unit was built from stainless steel, jacketed, beaker. Nozzles were attached at the bottom of jacketed beaker, through which emulsion was sprayed to form encapsulates. At the top of the unit openings were made for pressurized air, a mixing shaft, and a pressure release valve. Hoses were attached to upper and lower portions of beaker, through which water from a temperature controlled water bath flowed. This apparatus allowed for consistent indirect heat supply.

Kraton® 1650, which is a powdery substance, was converted to gel by mixing with mineral oil at 76.7° C. Wax was then added and a homogeneous isotropic liquid (continuous phase) was formed at 62.8° C. The emulsion was then prepared by emulsifying aqueous solution of sorbitol in the continuous phase. The resulting emulsion was a very stable emulsion: it did not phase separate for 24 hours at 60° C. Capsules were produced using the re-circulating encapsulation unit described in the previous paragraph.

| | Ingredient | Amount |
|---|---|---|
| Capsule formulation | | |
| Hydrophobic continuous phase | Mineral oil | 43.83% |
| | 1218 wax | 9.00% |
| | Kraton ® 1650 | 0.37% |
| Hydrophilic discontinuous phase | 70% Sorbitol solution | 46.80% |
| Curing solution | Water | 4000 g |
| | Neodol ® 25-9 | 20 g |
| | Silwet ® L-77 | 20 g |

The result was discrete, stable, round-shaped capsules, which did not stick together when they came in contact with one another and had an average size of about 1500 µm.

EXAMPLE 3

Kraton® 1702 and mineral oil mixture form a continuous phase (liquid gel) at room temperature, which allows for uniformed mixing of components. An emulsion encapsulating enzymes was prepared at room temperature, thus avoiding the use of any heat in the process. Components were mixed together at room temperature using an overhead Lightening® mixer.

| Mineral oil | 235.2 g |
|---|---|
| Kraton ® 1702 | 9.8 g |
| Properase ® 1600 L | 55.0 g |

The Kraton®/mineral oil mixture was transparent at room temperature. The enzyme in the sample of this emulsion was shown to have maintained activity. Capsules, however, could not be formed, in the absence of a hydrophobic solid.

EXAMPLES 4–7

Several capsule formulations, within the scope of the invention, were prepared, using the apparatus and process described in Example 2.

To simplify the preparation, a stock of 1.5% Kraton® 1650/mineral oil mixture (named "Kraton® 1650 gel" in the Tables and Examples below) was prepared by mixing and heating the mixture of 1.5 parts of Kraton® 1650 and 98.5 parts of mineral oil at 76.7° C. until it became an isotropic liquid.

| Capsule formulations | Ingredient | Amount |
|---|---|---|
| Example 4 | | |
| Hydrophobic continuous phase | 1.5% Kraton ® 1650 gel | 38.5% |
| | menthol oil | 15.3% |
| | 1218 wax | 7.7% |

-continued

| Capsule formulations | Ingredient | Amount |
|---|---|---|
| Hydrophilic discontinuous phase | 70 w/w % Sorbitol solution | 38.4% |
| | Blue Dye | 0.1% |
| Example 5 | | |
| Hydrophobic continuous phase | 1.5% Kraton ® 1650 gel | 39% |
| | 1218 wax | 10% |
| | Vitamin E | 15% |
| Hydrophilic discontinuous phase | 70 w/w % Sorbitol solution | 35.9% |
| | Blue Dye | 0.1% |
| Example 6 | | |
| Hydrophobic continuous phase | 1.5% Kraton ® 1650 gel | 39% |
| | 1218 wax | 10% |
| | Triclosan ® | 15% |
| Hydrophilic discontinuous phase | 70 w/w % Sorbitol solution | 35.9% |
| | Blue Dye | 0.1% |
| Example 7 | | |
| Hydrophobic continuous phase | 1.5% Kraton ® 1650 gel | 39% |
| | mineral oil | 15% |
| | 1218 wax | 10% |
| Hydrophilic discontinuous phase | 5.25% sodium hypochorite | 36% |

Examples 4–7 all resulted in discrete, stable, round-shaped capsules which did not stick together when they came in contact with one another. Capsules were stable (no leakage of encapsulated ingredient) for at least 3 months at 20° C.

EXAMPLE 8

It is highly desirable to have transparent capsules, but the capsules containing wax always exhibit opaqueness. This example demonstrates transparent capsules which were prepared within the scope of the invention.

| Capsule formulation | |
|---|---|
| Mineral oil | 133.0 g |
| Kraton ® 1650 | 7.0 g |
| 70% w/w sorbitol solution | 69.8 g |
| Hilton-Davis Blue AKS solution | 0.2 g |
| Curing solution | |
| Water | 495.0 g |
| Neodol ® 25-9 | 2.5 g |
| Silwet ® L-77 | 2.5 g |

Kraton® 1650 was mixed with mineral oil at about 82° C. until the mix became transparent gel. The blue AKS solution was pre-mixed with sorbitol solution and then emulsified in the Kraton® gel. The blue-colored emulsion was then cooled down and maintained at about 63° C. Capsules were prepared by dropping the emulsion by a pipette into curing solution, collected by a net and stored in a jar with curing solution. These capsules were round, fully transparent and colored blue. The capsule average size was about 2500 μm. After 24 hours, there was no dye leakage.

EXAMPLE 9

Enzyme capsules were prepared as follows.

An emulsion was prepared containing: 25 g Properase® 1600 L, 15 g of Sorbitol (70% aqueous solution), 8 g mineral oil, 13 g Bowax® 800, and 39 g of a gel which contained 1.5% Kraton® 1650 in mineral oil. The emulsion was prepared into capsules using a process of Example 8. Initial recovery after 15 minutes mixing was 100%. Stability of capsules after 3 days at 37° C. in a liquid detergent (as in Example 11, but without bleach capsules) was compared to the stability of non-encapsulated enzyme and was as follows:

| Sample | % Enzyme remaining |
|---|---|
| Detergent with encapsulated enzyme | 99 |
| Detergent with non-encapsulated enzyme | 0 |

EXAMPLES 10–11

Two liquid detergent compositions, within the scope of the invention, containing inventive capsules are as follows:

| Ingredients | Example 10 (g). | Example 11 (g). |
|---|---|---|
| Deionized water | 301.68 | 301.68 |
| 50% NaOH solution | 67.08 | 67.08 |
| 40% sodium xylene sulfonate | 42.59 | 42.59 |
| Linear Alkylbenzene Sulfonic acid | 242.41 | 242.41 |
| Neodol ® 25-9 | 107.62 | 107.62 |
| Coconut fatty acid | 14.20 | 14.20 |
| 47.1% sodium silicate | 81.63 | 81.63 |
| 40% Alcosperse ® 725 | 8.52 | 8.52 |
| Bleach capsules from Example 7 | 40 | 20 |
| Gum solution | | |
| Gellan | 0.45 | 0.31 |
| Hydroxypropyl methylcellulose | 0.00 | 0.45 |
| Deionized water | 90.05 | 89.74 |
| Miscellaneous | To 1000 | To 1000 |
| pH = 12.45 | | |

EXAMPLES 12–13

Two personal wash (liquid soap/shower gel) compositions, within the scope of the invention, containing inventive capsules are prepared as follows:

EXAMPLE 12

| Ingredients | % by wt. |
|---|---|
| Amphoteric (e.g., cocoamidopropyl betaine) | 15–20% |
| Anionic surfactant (e.g., sodium laureth sulfate) | 10–15% |
| Colored Vitamin E capsules of Example 5 | 2 |
| Humectants (e.g., glycerin) | 1–3% |
| Cationic polymers (e.g., polyquaternium) | 0.1–1.0% |
| Nonionic (e.g., PEG 80 Sorbitan monolaurate) | 1–3% |
| Sodium Hydroxide | 0.11 |
| Opacifier (e.g., styrenet acrylate) | 0.4 |
| Preservative (e.g., DMDM hydantoin) | 0.2 |
| Fragrance | 1.0 |
| Water | to 100.0 |

EXAMPLE 13

| Ingredients | % by wt. |
|---|---|
| Sodium Lauroamphoacetate | 7 |
| Sodium Laureth Sulfate | 14 |

-continued

| Ingredients | % by wt. |
|---|---|
| Cetyl Acetate And Acetylated Lanolin Alcohol | 0.5 |
| Lauric Acid | 2.5–3.0* |
| Sunflower Seed Oil | 3 |
| Colored Capsules of Example 8 | 1 |
| Cocamide Monoethanol amide | 2 |
| Glycerin | 2 |
| Guar Hydroxypropyl Trimonium Chloride | 0.5 |
| Citric Acid | 1.2 |
| Titanium Dioxide | 0.2 |
| DMDM Hydantoin/Iodopropynyl Butylcarbamate | 0.2 |
| EDTA | 0.002 |
| EHDP (Etidronic Acid) | 0.02 |
| Perfume | 0.5 |
| Water | to 100.0 |

EXAMPLES 14–15

Two liquid detergent compositions, within the scope of the invention, containing inventive capsules were prepared as follows:

| Ingredients | Example 14 (g). | Example 15 (g). |
|---|---|---|
| Deionized water | 301.68 | 301.68 |
| 50% NaOH solution | 67.08 | 67.08 |
| 40% sodium xylene sulfonate | 42.59 | 42.59 |
| Linear Alkylbenzene Sulfonic acid | 242.41 | 242.41 |
| Neodol ® 25-9 | 107.62 | 107.62 |
| Coconut fatty acid | 14.20 | 14.20 |
| 47.1% sodium silicate | 81.63 | 81.63 |
| 40% Alcosperse ® 725 | 8.52 | 8.52 |
| Bleach capsules from Example 7 | 40 | 20 |
| Enzyme capsules from Example 9 | 5 | 10 |
| Gum solution | | |
| Gellan | 0.45 | 0.31 |
| Hydroxypropyl methylcellulose | 0.00 | 0.45 |
| Deionized water | 90.05 | 89.74 |
| Miscellaneous | To 1000 | To 1000 |
| pH = 12.45 | | |

What is claimed is:

1. A capsule for incorporation into detergent or personal care compositions comprising:
   (a) a continuous phase comprising an isotropic mixture comprising:
      (a1) from about 0.1% to about 15%, by weight of the continuous phase, of a block co-polymer which is selected from the group consisting of a triblock co-polymer, radial co-polymer, and multiblock co-polymer, the co-polymer comprising at least one triblock having a structure: rigid block—flexible block—rigid block; and
      (a2) a hydrocarbon oil; and
   (b) from about 0.01% to about 45%, by volume of the capsule, of a discontinuous phase immiscible with the continuous phase,
   wherein the continuous phase surrounds the discontinuous phase.

2. A capsule for incorporation into detergent or personal care compositions comprising:
   (a) a continuous phase comprising:
      (a1) from about 0.1% to about 45%, by weight of the continuous phase, of a hydrophobic solid;
      and an isotropic mixture comprising:
      (a2) from about 0.1% to about 15%, by weight of the continuous phase, of a diblock co-polymer comprising at least one rigid block and at least one flexible block;
      (a3) a hydrocarbon oil; and
   (b) from about 0.01% to about 45%, by volume of the capsule, of a discontinuous phase immiscible with the continuous phase.

3. The capsule according to claim 1, wherein the continuous phase is transparent.

4. The capsule according to claim 1, wherein the co-polymer (a1) comprises polystyrene endblocks and elastomeric midblocks.

5. The capsule according to claim 1, wherein the co-polymer (a1) is selected from the group consisting of styrene-butadiene-styrene, styrene-isoprene-styrene, styrene-ethylene/butylene-styrene, and mixtures thereof.

6. The capsule according to claim 1, wherein the continuous phase further comprises from about 0.1% to about 60%, by weight of the continuous phase, of a hydrophobic solid.

7. The capsule according to claim 1, wherein the discontinuous phase is selected from the group consisting of an aqueous solution, an oil, an oil solution, an emulsion, a dispersion and a solid.

8. The capsule according to claim 1, wherein the discontinuous phase comprises an oil which is immiscible with the hydrocarbon oil in the continuous phase.

9. The capsule according to claim 1, wherein the discontinuous phase comprises an additional benefit agent and/or colorant.

10. The capsule according to claim 9, wherein the benefit agent is selected from the group consisting of a bleach, a bleach precursor, a surfactant, an enzyme, a whitening agent, a fabric softener, an anti-wrinkle compound, a dye fixative, dye transfer inhibitors, anti-redeposition polymers, soil release polymers, an anti-foam agent, a perfume, a silicone oil, a vegetable oil, a vitamin, a plant extract, a hydroxy acid, an anti-oxidant, an anti-bacterial agent, a moisturizer, and mixtures thereof.

11. A detergent composition comprising:
   (A) from about 0.01% to about 20%, by weight of the composition of a capsule comprising:
      (a) a continuous phase comprising an isotropic mixture comprising:
         (a1) from about 0.1% to about 15%, by weight of the continuous phase, of a block co-polymer which is selected from the group consisting of a triblock co-polymer, radial co-polymer, and multiblock co-polymer, the co-polymer comprising at least one triblock with a structure: rigid block—flexible block—rigid block; and
         (a2) a hydrocarbon oil; and
      (b) from about 0.01% to about 45%, by volume of the capsule, of a discontinuous phase immiscible with the continuous phase, and
      wherein the continuous phase surrounds the discontinuous phase;
   (B) a surfactant.

12. The detergent composition according to claim 11, wherein the continuous phase is transparent.

13. The detergent composition according to claim 11, wherein the composition is aqueous.

14. The detergent composition according to claim 11, wherein the discontinuous phase is an aqueous solution comprising from about 1% to about 10%, by weight of the detergent composition, of a bleach.

15. The detergent composition according to claim 11, wherein the composition is contained within the transparent package.

16. A detergent composition comprising:
   (A) from about 0.01% to about 20%, by weight of the composition of a capsule comprising:

(a) a continuous phase comprising:
  (a1) from about 0.1% to about 60%, by weight of the continuous phase, of a hydrophobic solid; and an isotropic mixture comprising:
  (a2) from about 0.1% to about 15%, by weight of the continuous phase, of a diblock co-polymer comprising at least one rigid block and at least one flexible block;
  (a3) a hydrocarbon oil; and
(b) from about 0.01% to about 45%, by volume of the capsule, of a discontinuous phase immiscible with the continuous phase;
wherein the continuous phase surrounds the discontinuous phase; and
(B) a surfactant.

17. A personal care composition comprising:
(A) from about 0.01% to about 20%, by weight of the composition, of a capsule comprising:
  (a) a continuous phase comprising an isotropic mixture comprising:
    (a1) from about 0.1% to about 15%, by weight of the continuous phase, of a block co-polymer which is selected from the group consisting of a triblock co-polymer, radial co-polymer, and multiblock co-polymer, the co-polymer comprising at least one triblock with a structure: rigid block—flexible block—rigid block; and
    (a2) a hydrocarbon oil; and
  (b) from about 0.01% to about 45%, by volume of the capsule, of a discontinuous phase immiscible with the continuous phase;
wherein the continuous phase surrounds the discontinuous phase; and
(B) a cosmetically acceptable vehicle.

18. The personal care composition according to claim 17 wherein the continuous phase is transparent.

19. The personal care composition of claim 17 wherein the composition is aqueous.

20. The personal care composition according to claim 17 wherein the composition is contained within the transparent package.

* * * * *